US 6,462,816 B1

(12) United States Patent
Doolen et al.

(10) Patent No.: US 6,462,816 B1
(45) Date of Patent: Oct. 8, 2002

(54) PARALLEL CAPILLARY ELECTROPHORESIS SYSTEM HAVING SIGNAL AVERAGING AND NOISE CANCELLATION

(75) Inventors: Robert D. Doolen, Sunnyvale, CA (US); Peijun Cong, San Jose, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 99 days.

(21) Appl. No.: 09/621,423

(22) Filed: Jul. 21, 2000

(51) Int. Cl.[7] .............................................. G01N 21/00
(52) U.S. Cl. ...................................................... 356/344
(58) Field of Search ................................. 356/344, 436, 356/440

(56) References Cited

U.S. PATENT DOCUMENTS

| | | | |
|---|---|---|---|
| 3,655,980 A | 4/1972 | Bossen | 250/83.3 D |
| 4,172,227 A | 10/1979 | Tyrer et al. | 250/461 B |
| 4,375,163 A | 3/1983 | Yang | 73/61.1 C |
| 4,576,477 A | 3/1986 | Corbet et al. | 356/39 |
| 4,618,769 A | 10/1986 | Johnson et al. | 250/338 |
| 4,747,686 A | 5/1988 | Sato | 356/72 |
| 4,833,332 A | * 5/1989 | Robertson, Jr. et al. | 250/458.1 |
| 5,003,488 A | 3/1991 | Hardy | 364/509 |
| 5,045,172 A | 9/1991 | Guzman | 204/299 R |
| 5,066,382 A | 11/1991 | Weinberger et al. | 204/299 R |
| 5,085,757 A | 2/1992 | Karger et al. | 204/299 R |
| 5,239,360 A | 8/1993 | Moring et al. | 356/344 |
| 5,274,240 A | 12/1993 | Mathies et al. | 250/458.1 |
| 5,303,021 A | * 4/1994 | Kita | 356/72 |
| 5,306,618 A | * 4/1994 | Prober et al. | 435/6 |
| 5,312,535 A | 5/1994 | Waska et al. | 204/299 R |
| 5,324,401 A | 6/1994 | Yeung et al. | 204/180.1 |
| 5,413,686 A | 5/1995 | Klein et al. | 204/299 R |
| 5,439,578 A | 8/1995 | Dovichi et al. | 204/299 R |
| 5,488,240 A | 1/1996 | Hlousek et al. | 250/231.16 |
| 5,582,705 A | 12/1996 | Yeung et al. | 204/603 |

(List continued on next page.)

FOREIGN PATENT DOCUMENTS

WO    WOX 99/42819    8/1999

OTHER PUBLICATIONS

Culbertson, C.T. et al., "Lowering the UV Absorbance Detection Limit in Capillary Zone Electrophoresis Using a Single Linear Photodiode Array Detector", *Anal. Chem.*, vol. 70, pp. 2629–2638, 1998.
Gong, Xiaoyi et al., "An Absorption Detection Approach for Multiplexed Capillary Electrophoresis Using a Linear Photodiode Array", *Analytical Chemistry*, pp. A–H, 1999.
Product Catalog, "Swagelok® BMS Series Bellows Sealed Metering Valves", Nupro Company, Feb. 1997.
Product Catalog, "Swagelok® Ultra–High–Purity Diaphragm Valve; DA Series", Nupro Company, May 1998.
Product Bulletin 640/641, "Electronic Pressure Controllers, 640 Series", MKS Instruments, Inc., Jul. 1995.

*Primary Examiner*—Michael P. Stafira
(74) *Attorney, Agent, or Firm*—Senniger, Powers, Leavitt & Roedel

(57) ABSTRACT

A multiplexed capillary electrophoresis system and process including a bundle of capillary tubes, a power source, a light source, a processor and an array of photodetector elements. Each element of the array generates a pixel signal corresponding to the light passing through the bundle of capillary tubes during the multiplexed capillary electrophoresis process. An A/D converter converts each of the pixel elements signals into a digital value corresponding to the light received by one of the photodetector elements. For each peak digital value, the processor selects five digital values corresponding to the light received by five contiguous photodetector elements and generates output signals. Each output signal corresponds to the light passing through the bundle of capillary tubes and is a function of the selected digital values. As a result, noise and drifts of the pixel signals are minimized.

23 Claims, 12 Drawing Sheets

U.S. PATENT DOCUMENTS

| | | | |
|---|---|---|---|
| 5,611,903 A | 3/1997 | Janssens et al. | 204/454 |
| 5,694,215 A * | 12/1997 | Carver | 356/246 |
| 5,695,626 A | 12/1997 | Yeung et al. | 204/605 |
| 5,730,850 A | 3/1998 | Kambara et al. | 204/603 |
| 5,741,411 A | 4/1998 | Yeung et al. | 204/452 |
| 5,900,934 A * | 5/1999 | Gilby et al. | 356/344 |
| 6,120,667 A * | 9/2000 | Hayashizaki et al. | 204/603 |

* cited by examiner

PARALLEL CAPILLARY ELECTROPHORESIS SYSTEM HAVING SIGNAL AVERAGING AND NOISE CANCELLATION

BACKGROUND OF THE INVENTION

This invention is generally in the field of capillary electrophoresis, and relates particularly to a system for and a method of processing the signals of a photodetector array of a multiplexed or "parallel" capillary electrophoresis system.

Capillary electrophoresis (CE) is a chemical separation technique involving the use of one or more capillary tubes.

Parallel CE, a recently developed technique using many parallel capillary tubes, is growing in popularity since this technology allows multiple samples to be analyzed quickly and efficiently. This is particularly advantageous in combinatorial chemistry where many hundreds and even thousands of samples are analyzed over a short period of time. Parallel CE involves the use of a "bundle" of capillary tubes, e.g., 96 such tubes. A chemical sample to be analyzed is loaded in each tube, and a high voltage is applied to the tube, causing the components of the sample to migrate in the tube at different speeds, thereby causing separation of the components which can then be analyzed by conventional light absorption or other techniques. For example, a photodetector array of linear elements may be used to sense the light passing through the bundle. Reference may be made to the following patents and publications for a more detailed description of CE, including parallel CE, and various analytical techniques used in CE: U.S. Pat. Nos. 5,900,934, 5,324,401, 5,312,535, 5,303,021, 5,239,360; C. Culbertson et al., Analytical Chemistry, 70, 2629–2638 (1998); and X. Gong et al., Analytical Chemistry, 7.2, A–H (1999).

The signals generated by elements of the photodetector array represent the separation of the components. Some of the signals represent light passing through the walls of the capillary tubes while other signals represent light passing between the capillary tubes and yet other signals represent light passing through the center of the capillary tubes. Some of these signals include more accurate information indicative of the separation of the components. In addition, the signals are subject to noise. There is a need for a system which processes signals to maximize the accuracy of the information embodied in the signals.

SUMMARY OF THE INVENTION

Among the several objects of this invention may be noted the provision of apparatus and method for optimizing the results of a capillary electrophoresis operation, particularly the clarity, resolution and/or detection limits of electropherograms generated during the operation; the provision of such an apparatus and method which average signals generated by elements of the array; the provision of such an apparatus and method which minimize long time drifts of signals generated by the elements of the array to generate a substantially flat baseline of the signals and which minimize short time fluctuations or other noise of such signals to generate an improved signal to noise ratio of the output signals; the provision of such apparatus and method which involve the use of conventional components for reduced cost; and the provision of such apparatus and method which are quick and easy to use.

In one form, the invention comprises a parallel capillary electrophoresis system for separating and analyzing the components of multiple chemical samples. A bundle of capillary tubes is arrayed to have at least portions of the tubes extending generally parallel to one another in a first plane. Each tube is adapted for the flow of a fluid sample therethrough. A power source applies a potential difference between inlet end portions and outlet end portions of the tubes to cause an electrical current to flow through the contents of the capillary tubes at a level sufficient to cause separation in the fluid samples. A light source emits light which passes through the capillary tube portions. A photodetector comprising a linear array of photodetector elements receives light passing through the capillary tubes, the light passing through each the capillary tube portions illuminating several photodetector elements. Each the photodetector element generates a pixel signal corresponding to the light received by the photodetector element. An analog to digital converter converts each of the pixel signals into a digital value corresponding to the light received by one of the photodetector elements. The improvement comprises a processor receiving the digital values and generating a plurality of output signals corresponding thereto. Each output signal is a function of at least two digital values corresponding to the light received by two photodetector elements, respectively, so that the output signals correspond to the light passing through the bundle of capillary tubes.

In another form, the invention comprises a method of processing a plurality of pixel signals, each generated by one element of an array of photodetector elements illuminated by light passing through a bundle of capillary tubes during a multiplexed capillary electrophoresis process. The method comprises the steps of:

converting each of the pixel elements signals into a digital value corresponding to the light received by one of the photodetector elements;

selecting, for each capillary tube, at least two digital values corresponding to the light received by two photodetector elements; and generating output signals corresponding to the light passing through the bundle of capillary tubes, each output signal being a function of the selected digital values.

Other objects and features will be in part apparent and in part pointed out hereinafter.

BRIEF DESCRIPTION OF THE DRAWINGS

Corresponding parts are designated by corresponding reference numbers throughout the several views of the drawings.

DETAILED DESCRIPTION OF THE PREFERRED EMBODIMENT

Figure 1:
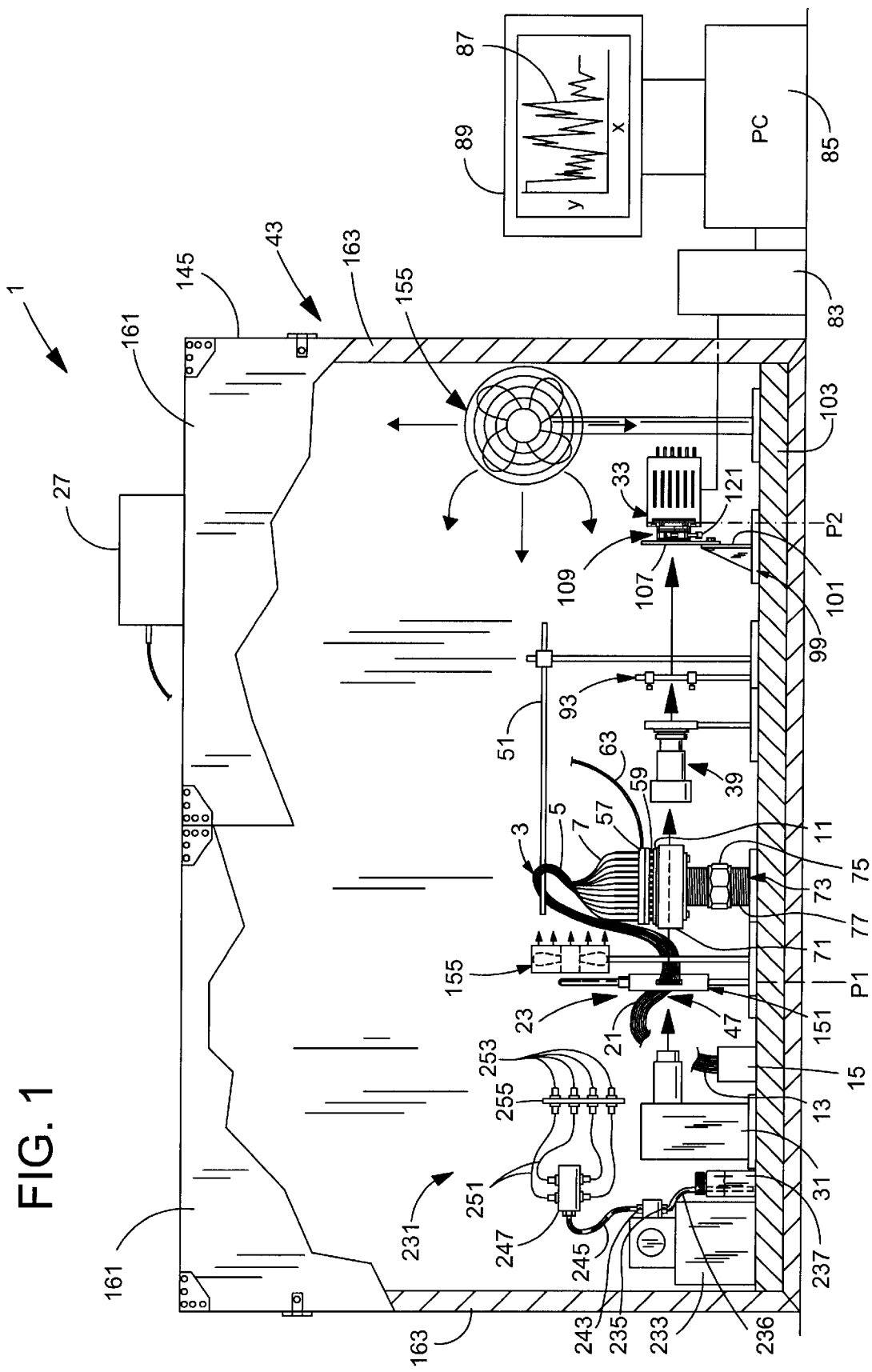
FIG. 1 is a schematic view of a parallel CE system.

Referring now to the drawings, FIG. 1 shows a multiplexed (parallel) capillary electrophoresis (CE) system, generally indicated at 1, for separating and analyzing the components of multiple chemical samples. The system may be for used for standard parallel CE or for parallel CE with chiral separation and comprises a bundle 3 of capillary tubes 5 having inlet end portions 7 spaced apart (e.g., spread out in a fanned formation) for loading of fluid samples to be analyzed from individual wells in a microtiter plate 11 into the tubes, outlet end portions 13 for exit of the fluid samples from the tubes into a waste receptacle 15, and intermediate portions 21 between the inlet and outlet portions arranged in a generally planar, ribbon-like array 23 in which the intermediate portions extend side-by-side in closely spaced generally parallel relation in a first plane P1. The system also includes a power source 27 for applying a potential (voltage) difference between the inlet end portions 7 and the outlet end portions 13 to cause an electrical current to flow through the contents of the capillary tubes 5, a light source 31 for emitting light to pass through the closely spaced array 23 of intermediate portions 21 of the capillary tubes, and a photodetector generally designated 33 comprising a linear array 34 of photodetector elements (35 in FIGS. 2 and 3) in a second plane P2 generally parallel to the first plane P1 for receiving light passing through the planar array of intermediate portions of the capillary tubes. Light passing through the tubes 5 is imaged on the photodetector 33 by an imaging lens, generally designated 39. In accordance with this invention, the system may also include a cooling system, generally indicated at 43, for dissipating the large quantities of heat generated in the capillary tubes 5 and contents thereof during a high-heat separation process, such as a chiral separation process.

More specifically, the capillary bundle 3 may comprise a series of 96 capillary tubes 5, although this number may vary. Each tube 5 is of relatively small diameter (e.g., 75 microns ID; 150 microns OD) and of a suitable electrically nonconductive material, such as fused silica so that high voltages can be applied across tube without generating excessive heat. The tubes 5 may have a polyimide coating which is removed by a laser beam, for example, in an area extending across the planar array 23 of intermediate portions 21 of the capillary tubes, thereby forming what may be referred to as a detection window 47 which is transparent or translucent so that light from the light source 31 can pass through the walls of the tubes at this location. Alternatively, the tubes can be transparent or translucent along their entire lengths, in which case no coating removal is necessary. The bundle 3 is of any appropriate length (e.g., 10 cm–2 m). At the detection window 47 the bundle 3 has a width, in a direction generally perpendicular to its length. As illustrated in FIG. 1, the bundle 3 may be supported above its inlet end portions 7 by a suitable support device 51. The capillary tubes 5 of the bundle 3 may be held in the aforementioned planar array 23 by any suitable means, such as by strips of adhesive tape (not shown) extending across the array on opposite sides of the detection window 47.

The microtiter plate 11 is supported by a thick insulating block 71 of dielectric material which is movable up and down relative to upper and lower metal power plates 57, 59 by a linear actuator generally designated 73. The power plates 57, 59 are connected to the power source 27 by suitable electrical cable 63. The actuator 73 is operated by rotating a nut 75 relative to a screw shaft 77 in one direction to extend the actuator and thus raise the insulating block 71 and microtiter plate 11, and in the opposite direction to retract the actuator and thus lower the block and microtiter plate. Alternatively, the actuator can be a power (e.g., pneumatic) actuator with suitable controls. The microtiter plate 11 has wells containing liquid samples of chemical compositions to be analyzed. Metal electrodes are secured (e.g., brazed) to the bottom face of a lower power plate 59 and extend down into the wells alongside the capillary tubes 5 for electrifying the contents of the wells when the power source 27 is activated. The power plates 57, 59 and electrodes are preferably of copper or other suitable metal, and the lower plate 59 and electrodes are preferably gold plated to render them chemically inert or non-reactive. To effect chiral separation, substantially more (3–5 times more) current must be used than in non-chiral separations. For example, for a bundle of 96 capillary tubes, a total current of 1–20 milliamps at a voltage of 5,000–30,000 volts may be required to effect chiral separation. A suitable power source for this application is Model 105–30R, available from Bertan High Voltage Corporation located in Hicksville, N.Y.

The light source 31 may be of any suitable type, such as a deuterium or tungsten lamp or a 254-nm mercury lamp, emitting light having a certain wavelength (e.g., 200–800 nm and generalizable to other wavelengths) corresponding to the absorption band of the sample components of interest. The light is typically ultraviolet or visible light.

Figure 2:
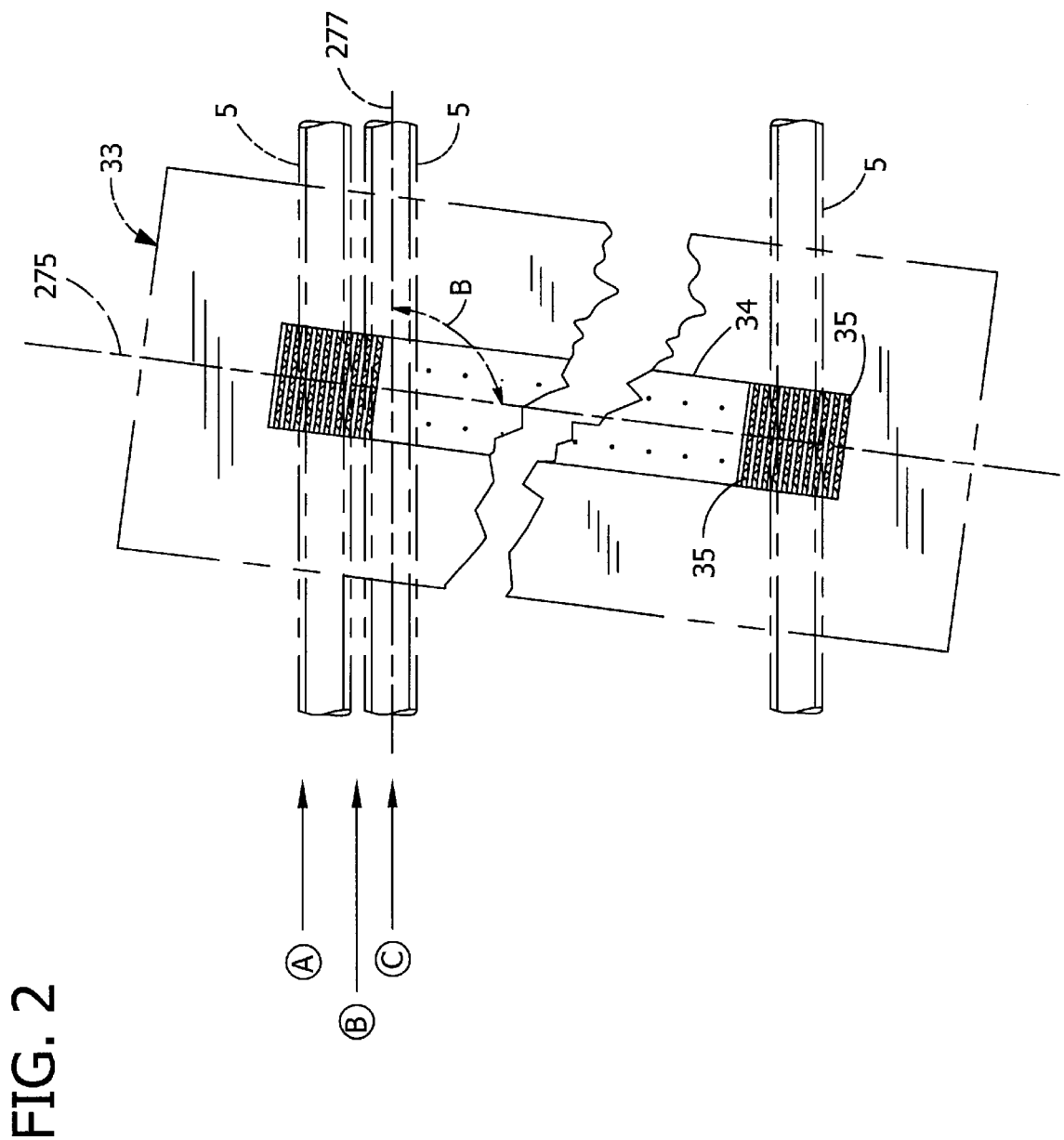
FIG. 2 is a view of a linear array of photodetector elements and an image of capillary tubes projected on the array, the linear array being skewed relative to the lengths of the tubes.
Figure 3:
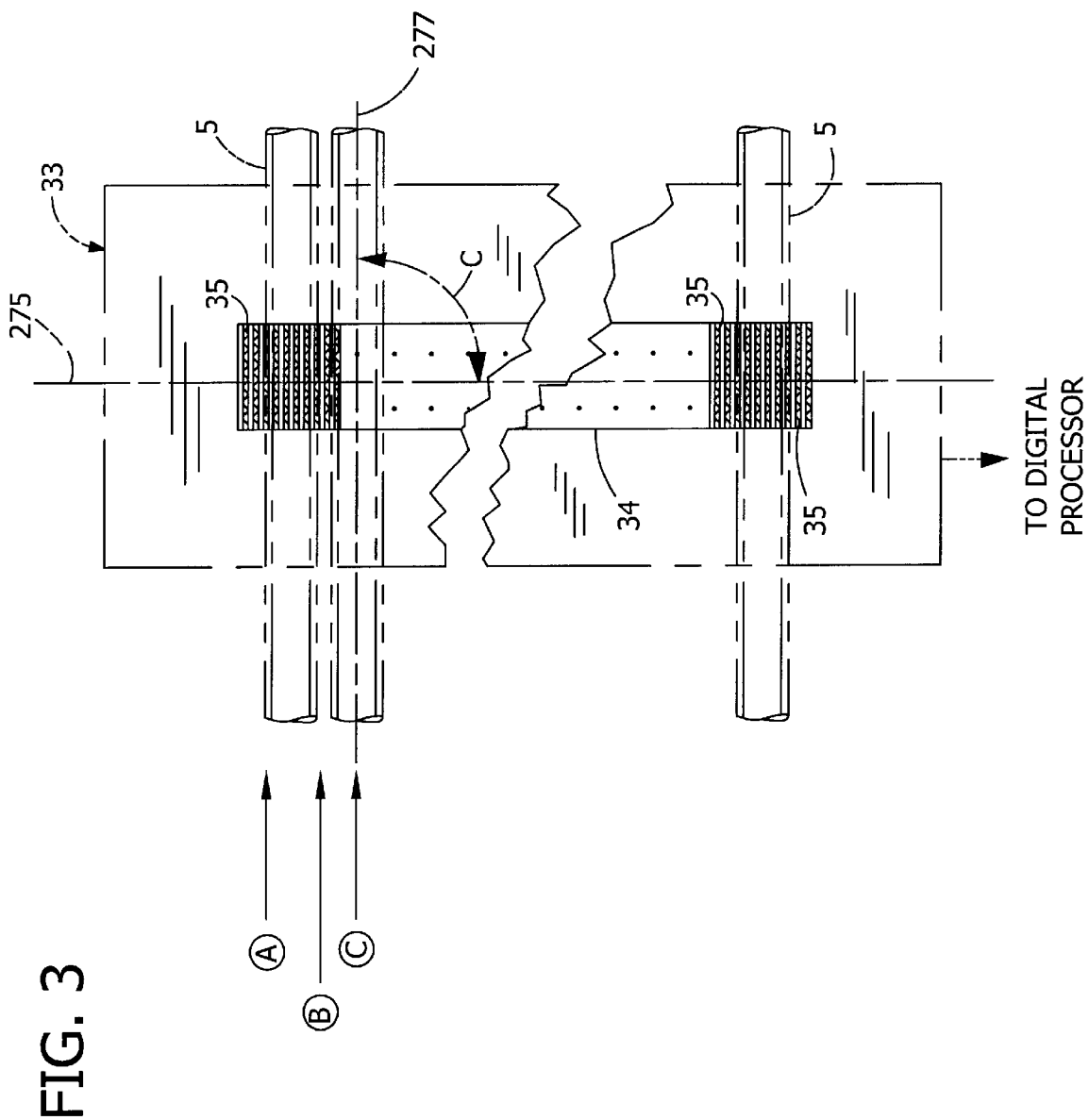
FIG. 3 is a view similar to FIG. 2 but showing the linear array rotated to a position generally perpendicular to the lengths of the tubes.

The photodetector 33 is of a conventional type, such as a photodiode device, having the aforementioned linear array 34 of photodetector elements 35 (FIGS. 2 and 3). These elements may be photodiodes, for example, arranged in one or more linear rows. For example, the photodetector 33 may be a model C5964 multichannel detector head by Hamamatsu incorporating a linear image sensor chip, a low-noise driver/amplifier circuit, and a temperature controller. In this example, the linear image sensor chip has 1024 diodes, each of which is 25 microns in width and 2500 microns height. Other types of photodetectors 33 can be used without departing from the scope of this invention. The photodetector elements 35 generate analog output signals, referred to herein as pixel signals which are then transmitted to a digital processor 83 (FIG. 1) and related equipment (e.g., a computer 85) for generating and displaying an electropherograms, i.e., a plot of light intensity versus time, as will be understood by those skilled in this field. This plot can then be evaluated to identify components of interest in the samples being analyzed. As shown in FIG. 1, the electropherograms 87 can be displayed on a screen 89 of the computer 85.

The imaging lens 39 may also be of conventional design, such as a quartz lens (Sodern; f.l.=94 mm; F=4.1) in combination with an interference filter 93 (Oriel) employed to define the absorption wavelength. The lens 39 is positioned between the detection window 47 and the photodetector 33 to receive light passing through the capillary tubes 5 and to image that light on the linear array 33 of photodetector elements 35. The image of the capillary tubes 5 projected by the lens 39 on the photodetector 33 may be an image 1.5 times actual size, for example.

Referring to FIG. 1, an optional mounting assembly, generally designated 99, is provided for mounting the photodetector 33 for rotation about a generally horizontal axis. This assembly 99 comprises a bracket 101 attached to the floor 103 of an enclosure, a vertical mounting plate 107 attached to the bracket and extending up from the bracket, and a rotational stage, generally designated 109, attached to the mounting plate. The rotational stage 109 comprises a stationary ring unit attached to the mounting plate 107, and a rotatable ring unit concentric with the stationary ring unit and rotatable relative thereto about the aforesaid horizontal axis A. The rotational stage 109 has a gross angular adjustment (e.g., a set screw arrangement not shown) whereby the rotatable ring unit can be quickly rotated to an approximate angular position, and a fine angular adjustment (e.g., a screw-type adjustment 121) whereby the angular position of the rotatable ring unit can be slowly moved to a precise position, the angular adjustment mechanism then functioning to hold or maintain the ring unit in such precise position until such time as further adjustment is required. Alternatively, a locking mechanism separate from the angular adjustment mechanism may be used to maintain the rotatable ring unit in its adjusted position. The vertical mounting plate 107 has a central opening therein aligned with the openings in the ring units. The type of rotational stage 109 shown in the drawings is generally of a type which is commercially available, e.g., Model UTR Series Manual Rotary Stage sold by Newport Corporation of Irvine, California.

Other types of rotational stages and/or mounting assemblies for the photodetector 33 may be used without departing from the scope of this invention. Also, the rotatable ring unit of the rotational stage 109 may be rotatable manually or by a suitable motorized mechanism.

Referring now to FIG. 1, the optional cooling system 43 of the present invention comprises a thermally insulated enclosure 145 enclosing the bundle 3 of capillary tubes 5, light source 31 and photodetector 33. The cooling system includes a first heat transfer mechanism comprising a conduction heat transfer mechanism, generally designated 151, for cooling the array 23 of closely spaced intermediate portions 21 of the capillary tubes, where the density of the tubes generates a substantial amount of concentrated heat which, unless dissipated, could cause solvent boiling and/or a change in solvent viscosity sufficient to diminish the quality of separation during electrophoresis. The cooling system also includes a second heat transfer mechanism comprising a pair of convective heat transfer units, each generally indicated at 155, for cooling the remaining portions of the bundle, including the inlet end portions 7 and outlet end portions 13 of the tubes 5 which, unlike the array 23, are spread apart and not closely packed.

The enclosure 145 can be in the shape of a large box, having front doors 161 for access to the interior of the enclosure. The enclosure is provided with a layer of thermal insulation 163.

FIG. 1 illustrates a system generally designated 231, for flushing the capillary tubes 5 and also for loading the tubes with a suitable buffer solution prior to conducting an actual sample separation process. The system 231 includes a pump 233 having an inlet 235 for selective connection via a line 236 to a first container 237 containing a supply of flushing solution (e.g., water or an aqueous solution of sodium hydroxide) or to a second container (not shown) containing a supply of buffer solution (e.g., cyclodextrin for chiral separation). The pump 233 has an outlet 243 connected via line 245 to a manifold 247 having a series of outlet ports. Each outlet port is connected to a conduit 251 which extends to one end of a fitting 253 mounted on a support 255 in the enclosure 145, the other end of the fitting being selectively connected to a group of capillary tubes. (For example, a capillary bundle consisting of 96 capillary tubes may be divided into eight groups 5a of 12 tubes each, and each group may be connected to a respective fitting 253.) The arrangement is such that the pump 233 may be operated to pump liquid from the appropriate container 237, 241 for delivery to the capillary tubes 5 via line 245, manifold 247, conduits 251 and fittings 253. The fittings are of conventional design and commercially available, e.g., from Valco Instruments Company Inc. of Houston, Texas.

In use, the CE system 1 of the present invention is set up as shown in FIG. 1, where the array 23 of the intermediate portions 21 of the parallel capillary tubes 5 lie in a first plane P1 within a channel of a cooling body of cooling mechanism 151, where the photodetector 33 is mounted on the rotational mount 109 in a position in which the linear array 34 of photodetector elements 35 lies in a second plane P2 generally parallel to the first plane P1, and where the axis of rotation is generally perpendicular to the two planes P1, P2. (As used herein, "generally parallel " includes an arrangement where the two planes P1, P2 are either exactly parallel or out of parallel with respect to one another by as much as about 15 degrees, and preferably only about 5 degrees. Similarly, "generally perpendicular " includes an arrangement where the axis A is either exactly perpendicular to a plane P1, P2 or off perpendicular by as much as about 7.5 degrees, and preferably only about 2.5 degrees.)

The capillary tubes 5 are cleaned ("conditioned") and prepared prior to the start of each sample separation run. This is accomplished by connecting the outlet end portions 13 of the groups of the capillary tubes 5 to respective fittings 253 on the support 255, and then operating the pump 233 to pump cleaning solution from the cleaning solution receptacle 237 through the capillary tubes, the flow being in a direction toward the inlet end portions 7 of the tubes. A microtiter plate 11 is positioned on the insulating block to receive cleaning solution as it exits the tubes. After the capillary tubes 5 have been flushed (e.g., "conditioned"), the inlet 235 of the pump 233 is connected to a container (not shown) containing buffer solution, and the pump is then operated to fill the capillary tubes with buffer solution. After the capillary tubes are properly cleaned and prepared, samples are loaded into the tubes. Sample loading is accomplished by disconnecting the outlet end portions 13 of the capillary tubes from their respective fittings 253 and placing the outlet end portions in a waste receptacle (not shown). A microtiter plate 11 containing the samples to be analyzed is positioned on the insulating block 71 with the capillary tubes 5 and electrodes extending down into the wells 9 of the plate. The power source is then operated to apply a voltage differential (e.g., 10 kv) across each capillary tube for a period of time (e.g., 10 seconds) suitable to cause the electro-kinetic movement of a quantity of sample from the wells 9 of the microtiter plate 11 into the inlet end portions 7 of the capillary tubes. After samples have been loaded into the capillary tubes, the microtiter plate 11 is replaced by a container of buffer solution so that the inlet end portions 7 of the capillary tubes extend down into the buffer solution.

The buffer solution container may be wrapped or otherwise sealed to reduce evaporation of the buffer.

Following sample loading, and prior to the start of an electrophoresis operation, the cooling system 43 is actuated to cool the interior of the enclosure 145 and the capillary tubes 5 therein. This involves actuating the two convective cooling units 155 and also the conduction cooling device 151 for a time sufficient to bring the interior air temperature of the enclosure 145 down to a temperature sufficient to prevent overheating of the capillary tubes and the contents thereof during chiral separation. A temperature in the range of 0–90° C., preferably in the range of 0–40° C., and most preferably about 20° C., is believed to be suitable for this purpose.

After the enclosure 145 and capillary tubes 5 are suitably cooled, a voltage is applied to the tubes, causing the various components of the samples to migrate at different speeds to effect separation, as will be understood by those skilled in this field. To separate chiral molecules, a relatively large current is required (e.g., a sum total of 750 milliamps for a bundle of 96 capillary tubes), which results in the generation of a substantial amount of heat in the tubes and contents thereof. The conduction heat transfer device 151 removes this heat in the area of the bundle 3 generally adjacent the detection window 47, where the capillary tubes 5 are relatively closely spaced. The convective heat transfer units 155 removes this heat from other portions of the bundle, including the inlet end portions 7 of the tubes 5. As a result, overheating of the capillary tubes and contents thereof is prevented, thus ensuring a more accurate analysis of the samples.

Light from the light source 31 passes through the planar array 23 of the capillary tubes and is projected by the lens 39 as an image of the tubes onto the photodiodes 35 of the photodetector 33. These diodes 35 generate pixel signals which are processed to generate and display an electropherograms 87 plotting light intensity (indicative of absorption levels) versus time. The clarity, resolution and detection limits of this plot can be improved by rotatably adjusting the rotatable ring unit(carrying the photodetector 33) of stage 109 to find the optimal angular position for providing an electropherograms having better clarity, resolution and/or detection limits. The adjustment procedure is best illustrated in FIGS. 2 and 3.

In FIG. 2, it will be observed that the image of the tubes 5 projected on the linear array 34 of photodiodes is at an angle where the longitudinal centerline 275 of the array is skewed at an angle B relative to the centerline 277 of a tube 5. This orientation does not yield an optimal electropherograms, since the photodiode elements 35 are slanted relative to the lengths of the tubes. The characteristics (clarity, resolution and/or detection limits) of the electropherograms can be improved by rotating the rotatable ring unit 115 of the rotational stage 109, and the photodetector 33 mounted thereon, to the position shown in FIG. 3 where the photodiode elements 35 are more aligned with the projected image of the tubes 5. The optimal angle, indicated at C in FIG. 3, is usually about 90 degrees, that is, an angle where the longitudinal centerline 275 of the linear array 34 of photodetector elements 35 is precisely perpendicular to the capillary tubes (i.e., the projected image of the tubes) and the longitudinal centerlines of the elements 35 are parallel to the longitudinal centerlines 277 of the capillary tubes. The optimal angle is identified by rotating the rotatable ring unit one way or the other until the display of the electropherograms 87, as it appears on the screen 89, is optimal in terms of clarity, resolution and/or detection limits. The ring unit 115 is then maintained in this position throughout the separation process. The precise position of the rotatable ring unit relative to the stationary ring unit can be recorded by using the markings on the two units.

It will be understood from the foregoing that the system described above optimizes the results of a parallel CE operation by improving the clarity, resolution and/or detection limits of electropherograms generated during the separation and analysis process. This is achieved by a method involving rotating the photodetector 33 relative to the projected image of the capillary tubes to a position in which the array 34 of photodetector elements 35 is at an optimal orientation (e.g., as shown in FIG. 3), relative to the image, and then maintaining the photodetector in such position. The optimal orientation is easily determined simply by watching the electropherograms while rotating the photodetector 33 until the display of the electropherograms is optimal.

It will also be observed that the cooling system 43 of this invention will provide efficient well-regulated cooling of the bundle 3 by using the convective and conductive heat transfer devices 151, 155, the conductive device providing additional cooling of the tubes 5 where they are more closely spaced in the area adjacent a window in a body where the samples in the tubes 5 are exposed for CE analysis. Consequently, even during chiral separation and other CE processes generating large amounts of heat, the temperature of the samples will remain well below boiling to avoid the formation of bubbles in the samples which can cause dielectric breakdown, sparking and other undesirable results adversely affecting sample analysis. The system of the present invention can be used for any parallel or multiplexed CE process, including but not limited to the separation of chiral molecules. It is believed that the system described above is the first parallel CE system designed to effect chiral separation.

Chiral separation using parallel CE can be effected with or without the use of circular dichroism ("CD") which is the differential light absorption properties of left and right circularly polarized light and which is a characteristic spectroscopic property of chiral molecules. When CD is used, the throughput can be greatly improved because the separation of enantiomers is not required resulting in a shorter separation/detection times. CD can be used to quantitatively identify enantiomeric excess in the presence of both enantiomers of a chiral species. The system described above can be modified to use CD by placing a photoelastic modulator between the light source 31 and the detection window 47 of the capillary tubes. The modulator modulates the light between the left and right circularly polarized components. The magnitude of the CD signal is determined by taking the difference between the left and right hand signals at the photodetector 33. CD is commonly determined for absorption but can also be determined from a fluorescence signal in a fluorescence detection (rather than light absorption) system. In such a system, an analyte which emits upon illumination (either naturally or via a chemical tag) can be used. In this case, an intense source, lamp or laser, illuminates the capillary array and the resulting emission is detected by the diode array.

While the cooling system of the present system is an important aspect, it is contemplated that cooling of the bundle 3 during parallel CE may not be necessary under all circumstances, in which case the cooling devices 151, 155 and/or enclosure 145 may be eliminated.

With regard to the above, the disclosures in co-pending, co-assigned U.S. patent application Ser. No. 09/621,890, filed Jul. 20, 2000, entitled a Multiplexed Capillary Electrophoresis System For Chiral Separation, and co-pending, co-assigned U.S. patent application Ser. No. 09/619,945, filed Jul. 20, 2000, entitled a Multiplexed Capillary Electrophoresis System with Rotatable Photodetector, are both incorporated herein by reference in their entirety.

SIGNAL PROCESSING

Figure 4:
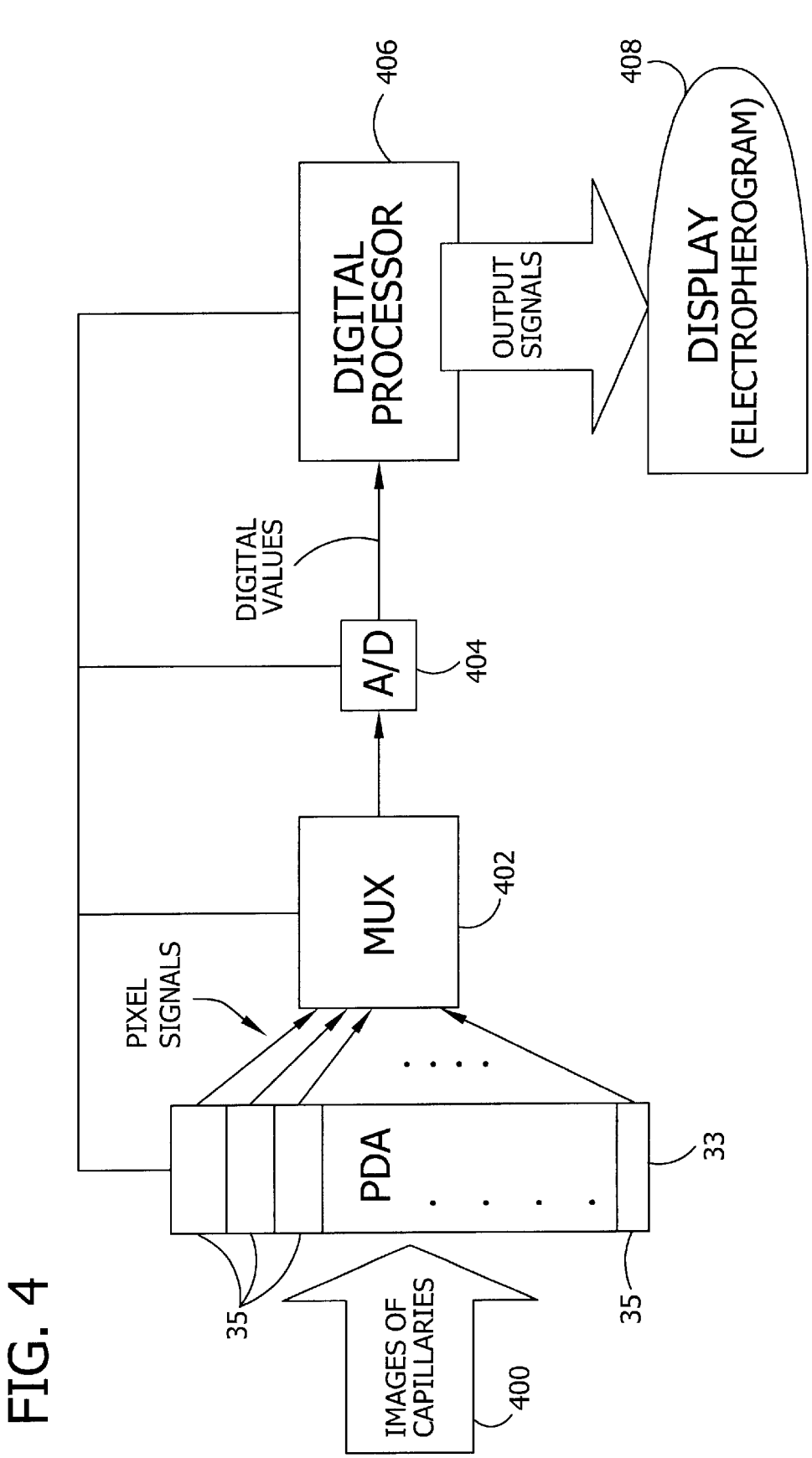
FIG. 4 is a block diagram of a photodetector array and processing circuitry of a parallel CE system of the invention.

Referring now to FIG. 4, the images 400 of the capillaries on the PDA 33 can be examined by looking at each pixel element 35 of the PDA 33. Each pixel signal generated by each element 35 is provided to a multiplexer 402 which sequentially provides the pixel signals to an analog-to-digital (A/D) converter 404. The pixel signals are converted to digital values corresponding to the light received by each of the elements 35. The digital values are provided to digital processor 406 which receives each of the digital signals and generates a plurality of output signals corresponding thereto. The processor is programmed, as noted below, so that each output signal is a function of at least two digital values corresponding to the light received by two different photodetector elements, respectively. In particular, each output signal is a function of at least two digital values corresponding to the light passing substantially simultaneously concurrently through two different photodetector elements 35. Optionally, the output signals may also be a function of the average over time of the sequence of digital values. As a result, each output signal corresponds to the light passing through the capillary tube portions. The output signals are provided to a display 408 which displays an electropherograms.

Figure 5:
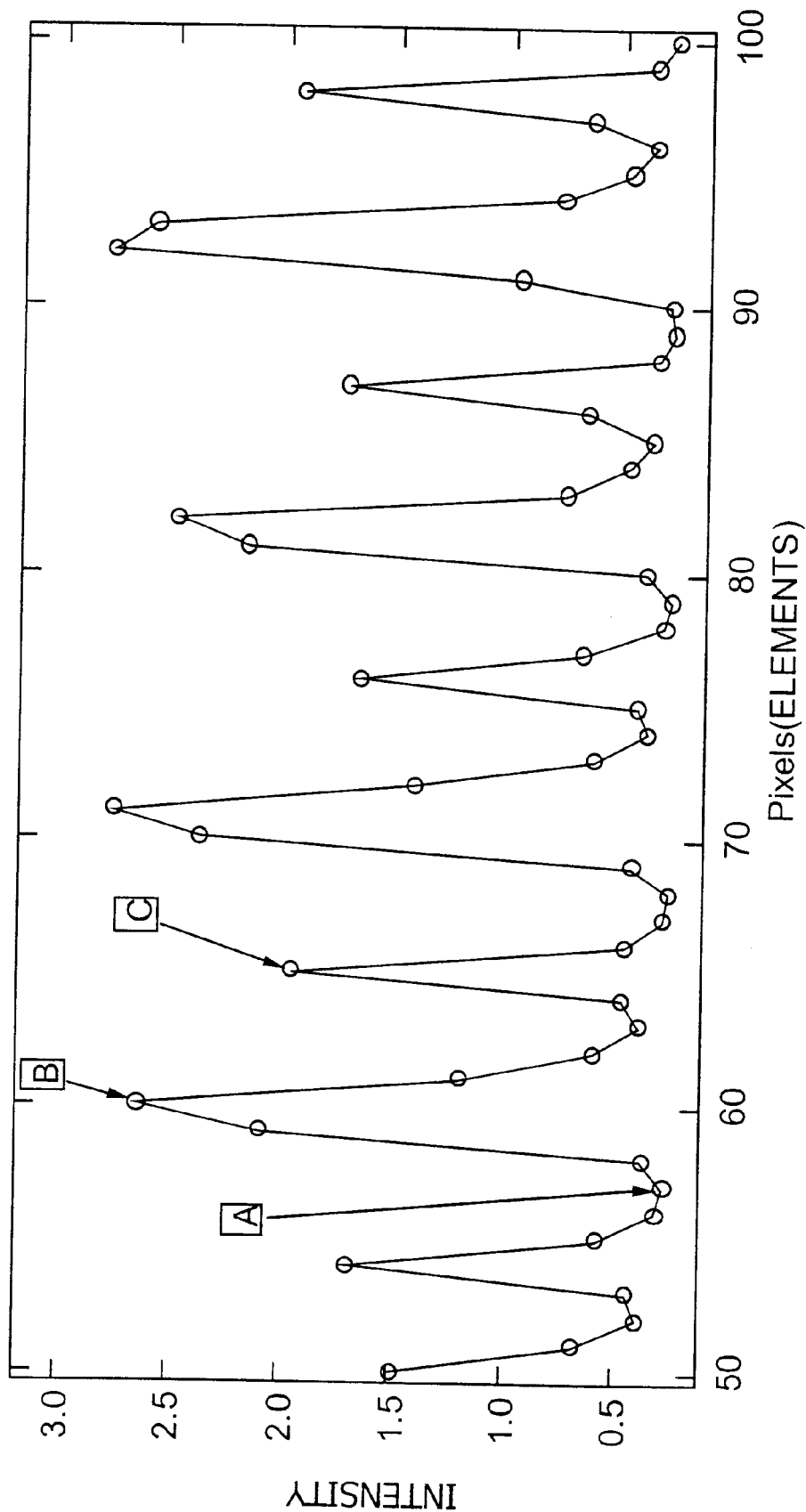
FIG. 5 is a plot of the intensity of the pixel signals along the vertical y-axis as a function of the position along the horizontal x-axis.

FIG. 5 shows a plot of a sampling of the pixel signals from the PDA elements 35 corresponding to a typical section of the capillaries imaged onto the PDA 33. The value for each individual pixel is designated by an open circle (o) and has been connected together by straight lines to illustrate the varying values of the pixel signals from pixel to pixel or element to element. FIG. 5 shows that the pixel signals for pixels (or elements) 50–100 vary in light intensity from about 0.2 to 2.8, based on the vertical scale along the y-axis which is proportional to light intensity.

There are three features of the plot of FIG. 5 to notice: the repetition of a minima and two maxima. There are pixels having a magnitude which constitute a local minima A. These pixels represent areas were little or no light is being detected. For example, the pixels labeled A represent areas where light is traveling through the sides and side-walls of the capillaries to the detector (see FIGS. 2 and 3). There are also two types of local maxima, B and C. The pixels labeled B (i.e., primary maxima) have a much larger magnitude than the pixels labeled C (i.e., secondary maxima). Pixels B represent areas where the light passes between the capillaries and is unimpeded to the detector. The pixels labeled C represent areas where light is traveling through the central areas of the capillaries to the detector (see FIGS. 2 and 3). The pixels labeled C are those that carry the useful information.

To observe the eluting species, one preferably observes peak C as a function of time. Previously, it has been reported that one should use the single pixel C at the maximum peak for data interpretation (e.g., Gong et. al., cited above). In particular, it has been suggested that successive pixels C over time each have the best signal to noise ratio. It has been found that one can obtain superior data quality data by averaging adjacent pixels. In general, the processor according to the invention selects one peak digital value (e.g., pixel B and/or pixel C) and averages the selected digital value with at least one other digital value to generate averaged values which are used to generate the output signals to the display. As a result, the output signals are a function of the averaged values as explained below in more detail. Preferably, the selected peak digital value is averaged with four (4) contiguous or adjacent values. Ideally, the selected values constitute pixels B. However, it has been found that superior results are obtained when the selected values include both pixels B and pixels C. Optionally, the digital values (which are part of a sequence over time from each element 35) may be averaged over time before averaging with contiguous/adjacent pixel values or the averaged contiguous/adjacent pixel values may be averaged over time after the averaged values are calculated by the processor.

It is believed that superior data is not simply a manifestation of signal averaging but that there is a correlation of the noise on adjacent pixels. The correlation can be seen in the long time drifting of the signal and in short time fluctuations, as noted below. These phenomena may be attributed to the capillary image moving between adjacent pixels. As a result, the peak pixels are selected and processed as noted herein to minimize long time drifts so that a substantially flat baseline of the output signals is generated. Also, the peak pixels are selected and processed as noted herein to minimize noise so that an improved signal to noise ratio of the output signals is generated.

Figure 6:
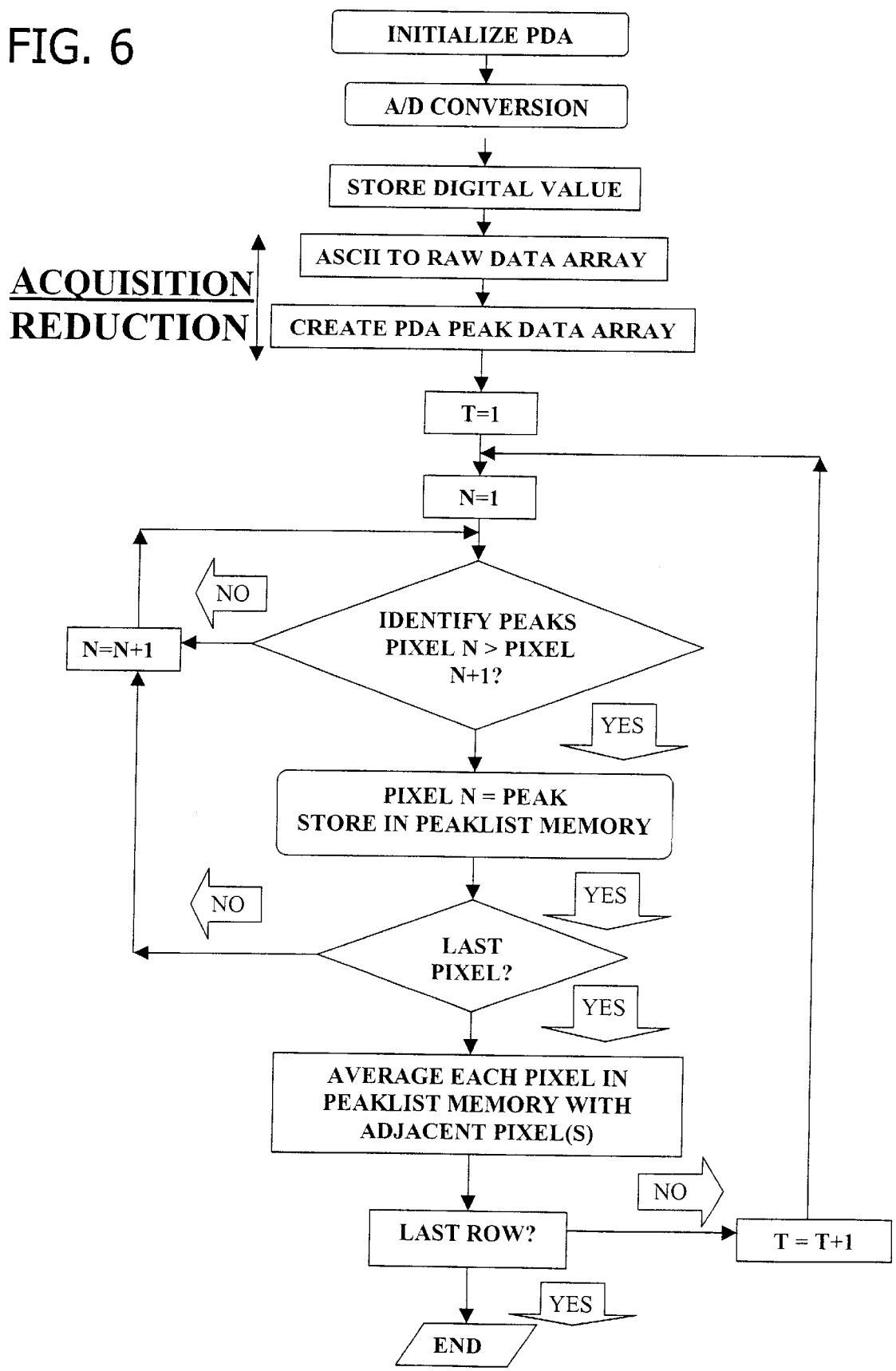
FIG. 6 is a flow chart of the steps employed by a processor of the invention to generate output signals.

FIG. 6 is a flow chart of the steps employed by a processor of the invention to generate output signals by averaging adjacent or contiguous pixels. As used herein, adjacent pixels mean contiguous and/or non-contiguous pixels. The software operating the processor 406 includes data acquisition software having a functionality as depicted by the upper portion of FIG. 6. The data acquisition software starts by initializing the PDA 33 at step 601. The software instructs the processor to output two signals for the driver/amplifier circuit on the PDA 33 via a National Instruments A/D board (not shown). The first signal is a master clock frequency (CLK) and the second signal is a start pulse (START). The CLK signal determines the readout frequency of the PDA output as read by the multiplexer 402. The START pulse determines the integration time of the signal on the PDA 33. The START pulse is synchronized to the CLK frequency. Preferably, the CLK frequency is set to the maximum value allowed by the hardware, e.g., 375 kHz. The START pulse must be longer than one cycle of the CLK frequency. Preferably, the user chooses the START pulse duration such that the signal on the PDA 33 is approximately 85% of saturation.

Next, the data acquisition software waits for a trigger signal from the PDA 33 (and multiplexer 402) indicating the beginning of a sequential read of the 1024 elements by the multiplexer 402. When the trigger is received, an A/D conversion is performed at 603 by the A/D converter 404 of the National Instruments board. The processor 406 stores the digital output in a 1×1024 memory array, one number for each pixel of the PDA 33. The data acquisition software then waits for the next trigger from the PDA 33 indicating the beginning of the next sequential read of the 1024 elements. Each sequential read of the elements of the PDA 33 is added the 1×1024 memory array to increase the value of each element in the storage array. In other words, successive reads of the PDA 33 are summed and stored in the one-dimensional 1×1024 array. The number M of PDA reads to be summed for each time step is determined by the user. Preferably, this number is chosen to reduce the amount of data to one digital value for each PDA element per second.

After the number M of PDA reads has been reached, each digital value in the 1×1024 array is divided by the number of reads M and stored as the nth row of a 1024×T array for T time steps. This process averages the signal reads for each time step (e.g., "box car" averaging). At the end of the run, the 1024×T array is stored as a ASCII file by step 605.

Preferably, during this process the display 408 shows three things: the controls and indicators for the various parameters, a graph of the PDA signal versus pixel and a strip chart type display of the signal from a single pixel as a function of time.

The software also includes data reduction software having functionality as depicted by the lower portion of FIG. 6. The data reduction software may be a completely separate piece of software from the data acquisition software or the two may be integrated into a single package. The first step 606 reads the ASCII file data. The data is read from a user chosen file and stored in a 1024×T array, referred to as the raw data array, where T is the number of time points taken during the run. Next, peak data at a given time is extracted from the raw data array at 607 to create a PDA peak data array. To do this, the second row is stored in a 1024 element array, referred to as the PDA peak data array. In other words, the 1024 elements of the PDA array are column [0] row [2] through column [1023] row [2] of the raw data array. The PDA peak data array may be saved as a separate file (e.g., "pda.dat") for viewing later in a commercial graphing package.

The PDA peak data array is created by steps 609–621 to identify peaks that correspond to capillaries or open spaces in the capillary array. There is no need to differentiate between these two peaks although this differentiation may be desirable for certain data. The peaks are identified by finding every local maxima (both primary and secondary maxima) in the raw data array as follows. For each time point (1 to T; see step 609) and for each element (N=1 to 1024; see step 611), the relative peak signals are identified at step 613 by comparison to the previous digital signals in the raw data array. Ideally, one would get 191 peaks corresponding to the 96 capillaries and the 95 spaces between the capillaries. The PDA peak data array is a list of the identified peaks and may be saved at steps 615, 617 as an array, peaklist, such as file "peaklist.dat."

The peaklist is used to generate reduced data. It is this data that is viewed as the electropherograms. At step 619, for each digital pixel signal (N) corresponding to a PDA element in the peaklist array, the digital signal value in the array is summed with the two elements of lower pixel number (N−1 and N−2) and the two pixels of higher pixel number (N+1 and N+2) at a given time step. The sum is then divided by five and is saved as the point for that time step in an array for the pixel from the peaklist array. As an example, the first pixel in the peaklist might be pixel 7. The program starts at the first time step. It sums pixel 5, 6, 7, 8 and 9, divides the sum by five and saves that averaged value as the first point in an array for the peak found at pixel 7. This is done for each peak in the peaklist and for each time step. For a run that is T time steps that had 191 pixels identified as peaks for each time step, the program will produce 191 arrays that are T elements long. Each one of these arrays may then be saved to a single file that the user names. A commercial graphing program can then identify each of these arrays and plot them separately. The user can then identify the capillaries from the spaces and evaluate the data by hand.

Figure 7:
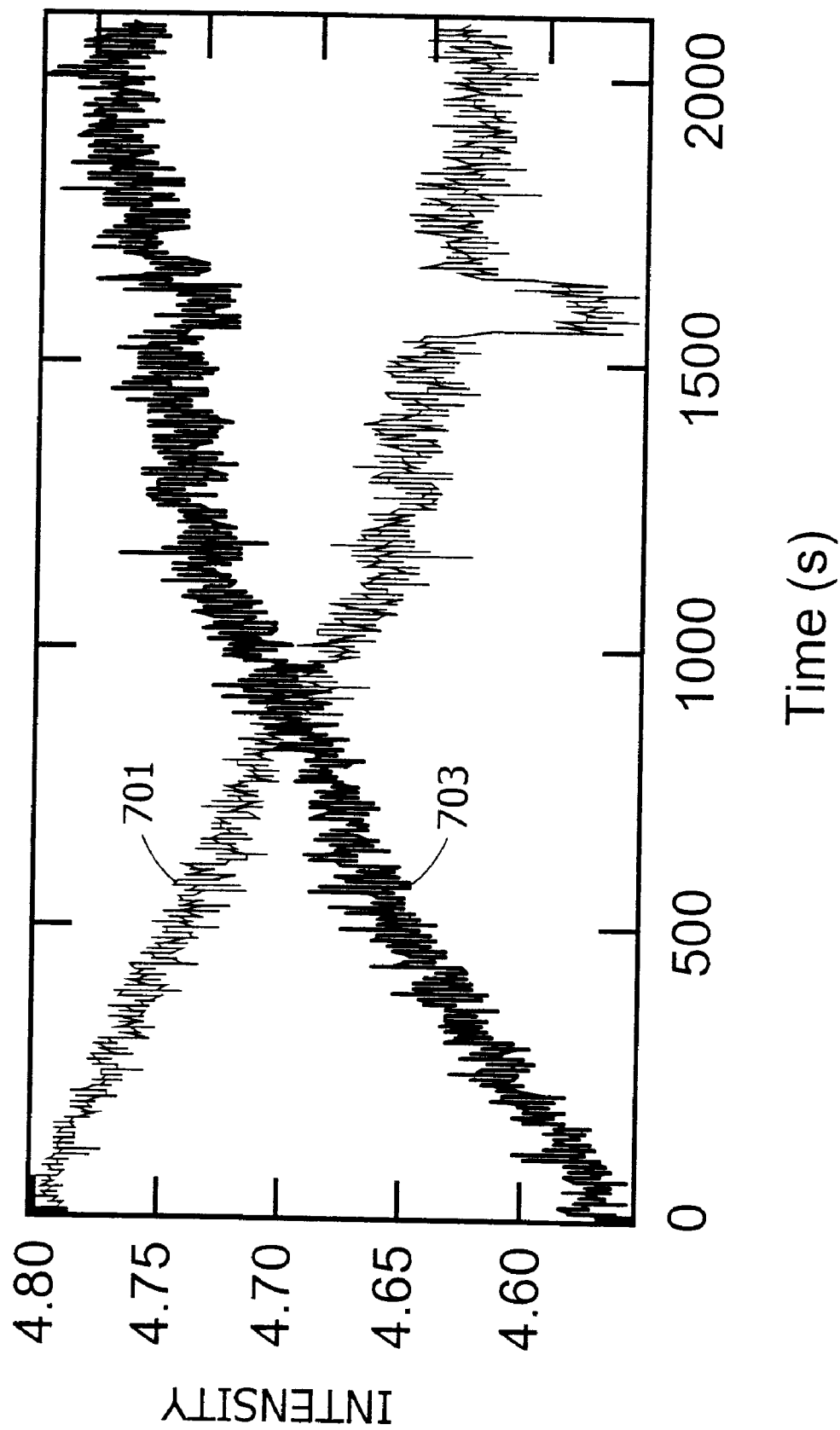
FIG. 7 is a plot of the intensity (y-axis) over time (x-axis) of the maxima pixels and of an adjacent pixel from one side.
Figure 8:
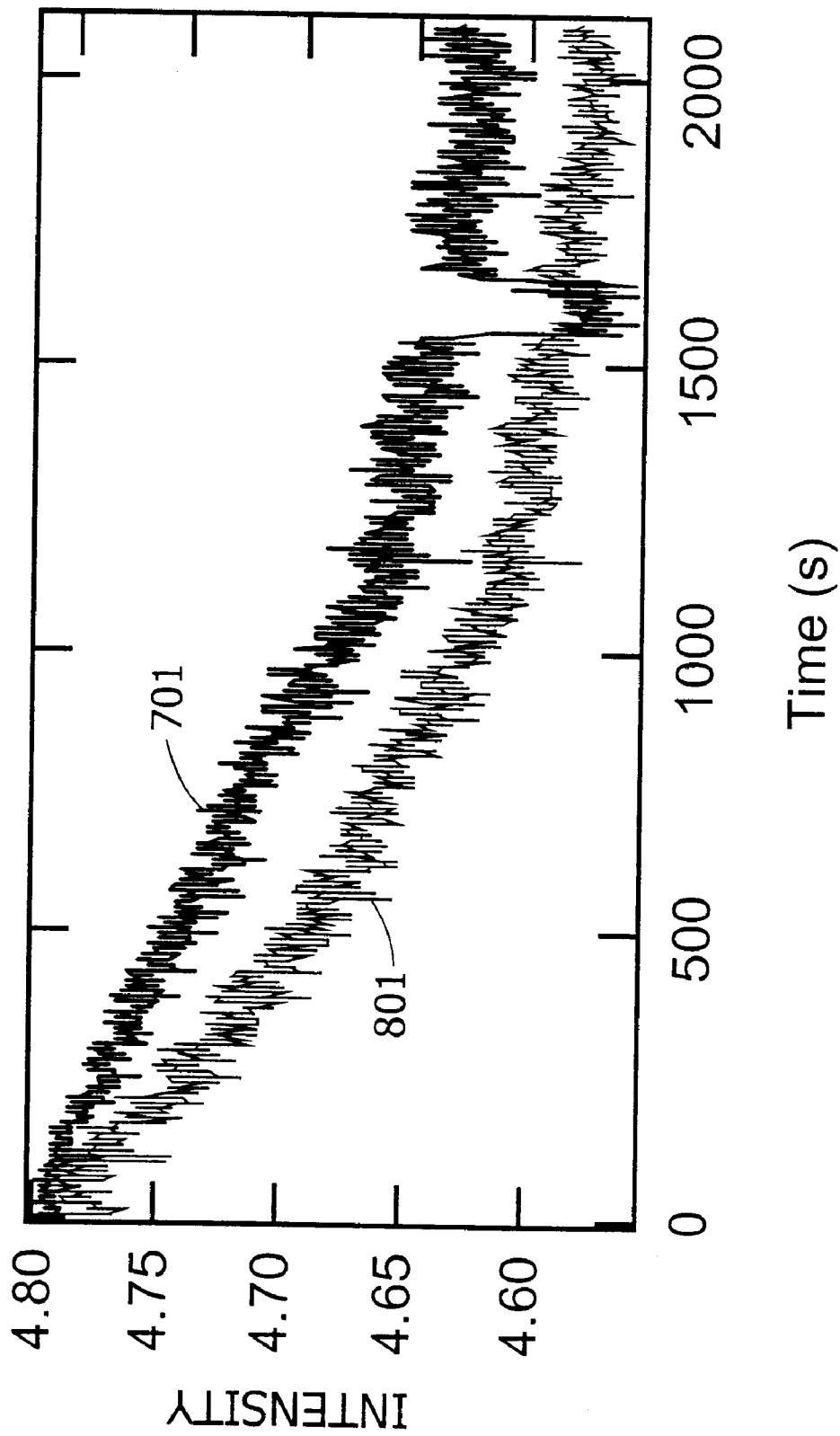
FIG. 8 is a plot of the intensity (y-axis) over time (x-axis) of the maxima pixels and of an adjacent pixel from the other side.

It has been found that the pixel intensity values are subject to a long time drift. This long time drift can be seen in FIGS. 7 and 8 which illustrates digital pixel signals as a function of time along the x-axis. FIG. 7 illustrates a waveform 701 over time of the digital signals from one peak pixel and a waveform 703 over time of the digital signals from a second pixel adjacent to one side of the peak pixel. It can be seen that these waveforms are anti-correlated. In FIG. 8, the waveform 701 of the digital signals from the same peak pixel is shown along with a signal 801 of the digital signals from a third pixel adjacent to the other side of the peak pixel. These pixel signals in FIGS. 7 and 8 exhibit the same long time drift. It is believed that this drift may be due to the capillaries relative position drifting over the duration of the run. The drift is moving toward one side causing the signals of the second pixel to increase while causing the signals of the third pixel to decrease.

Figure 9:
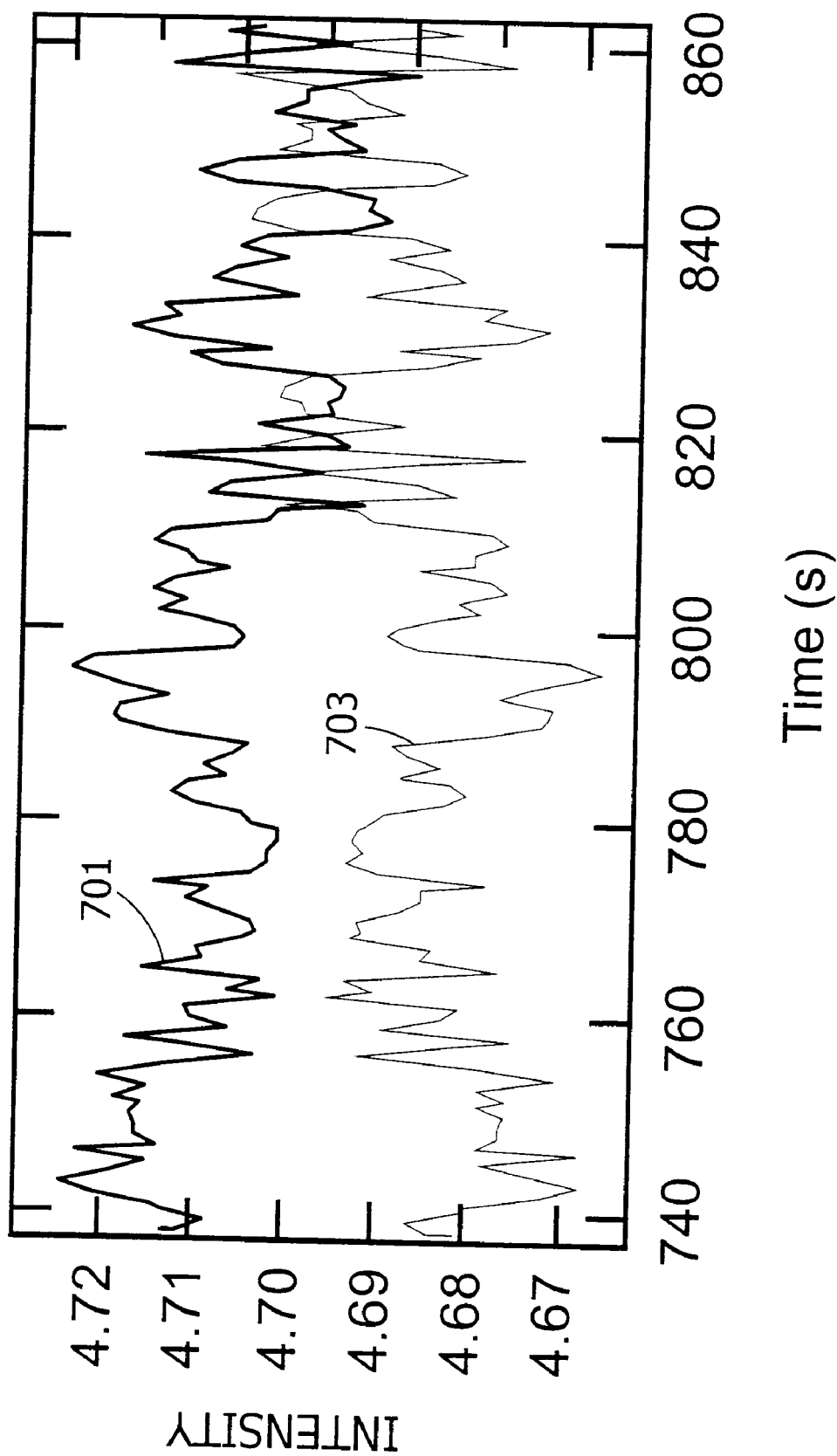
FIG. 9 is an exploded plot of the plot of FIG. 7 showing the short time scale behavior.
Figure 10:
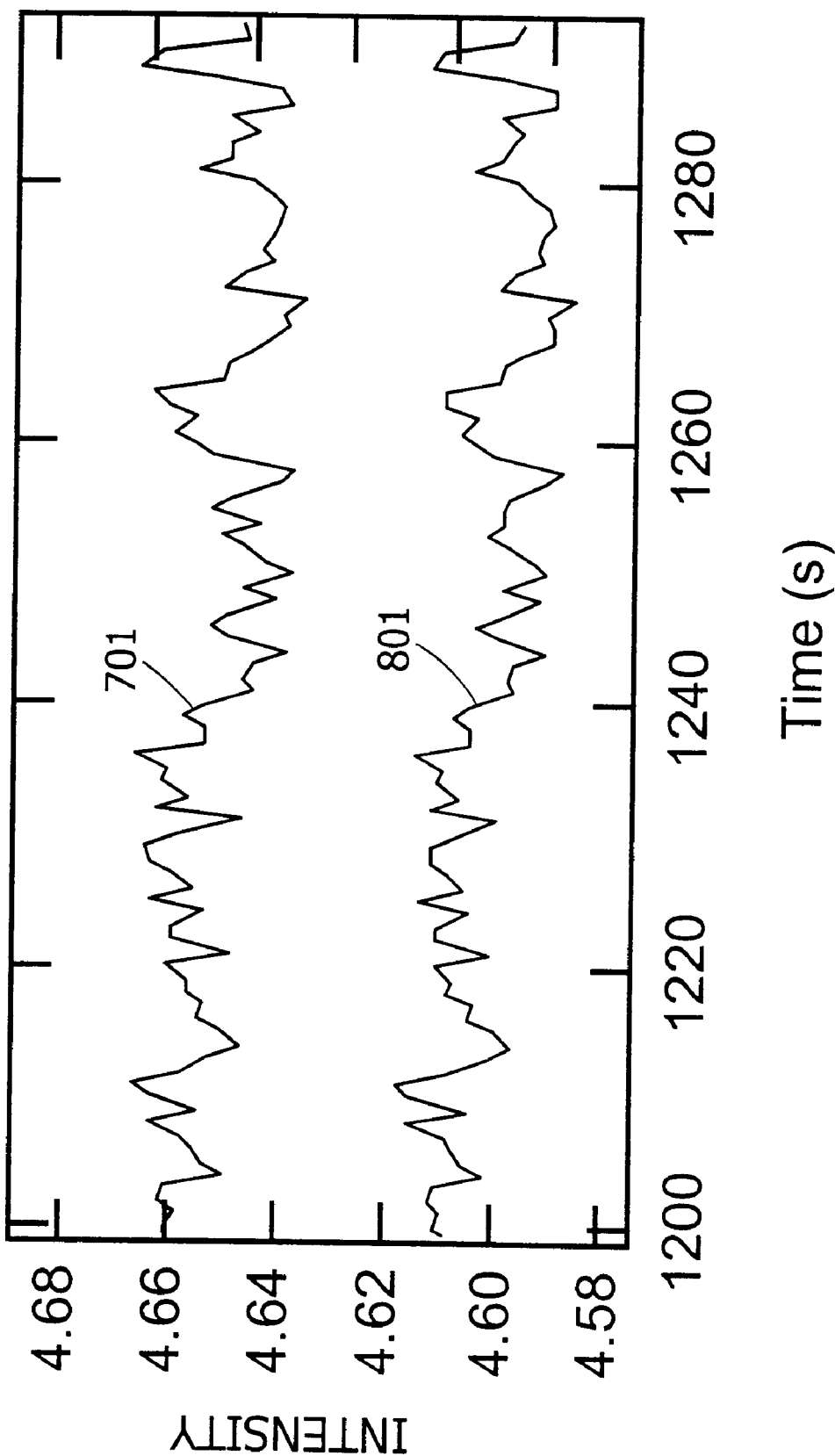
FIG. 10 is an exploded plot of the plot of FIG. 8 showing the short time scale behavior.

Similar short time behavior can be seen in FIGS. 9 and 10 which are the same as FIGS. 7 and 8 with a small section expanded to show the short time fluctuations. In FIG. 9, it can be seen that the noise is anti-correlated, as the waveform 701 of one pixel goes up, the waveform 703 of the other pixel goes down. This is the same trend as observed in the long time drift of FIGS. 7 and 8. In FIG. 10, the noise is correlated, similar to the long time drift. This behavior is most likely due to fluctuations in the capillary position on a time scale similar to that of the data collection rate, 1 point per second.

Figure 11:
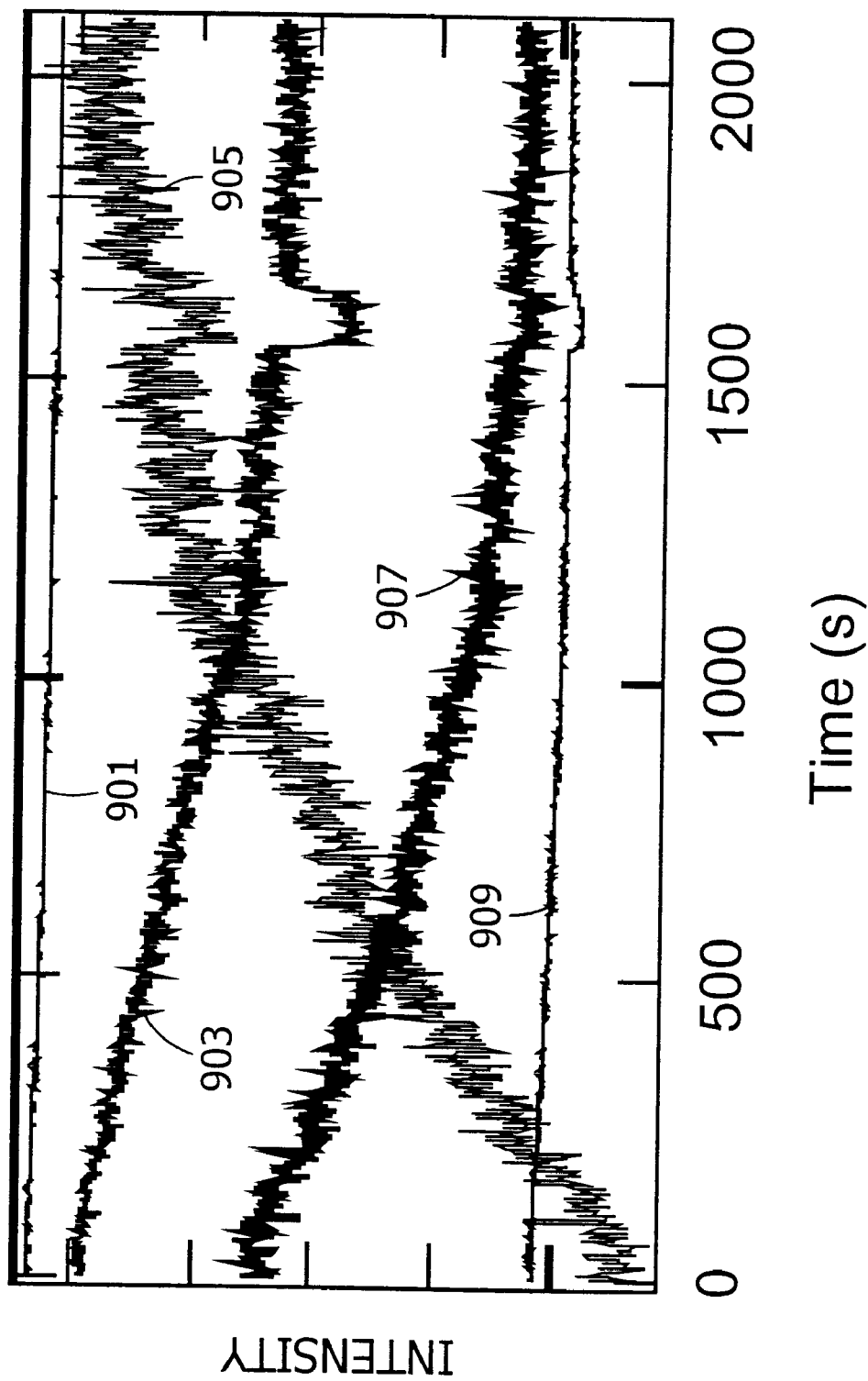
FIG. 11 is a plot of the intensity (y-axis) over time (x-axis) of five (5) adjacent pixels centered around each maxima pixel.
Figure 12:
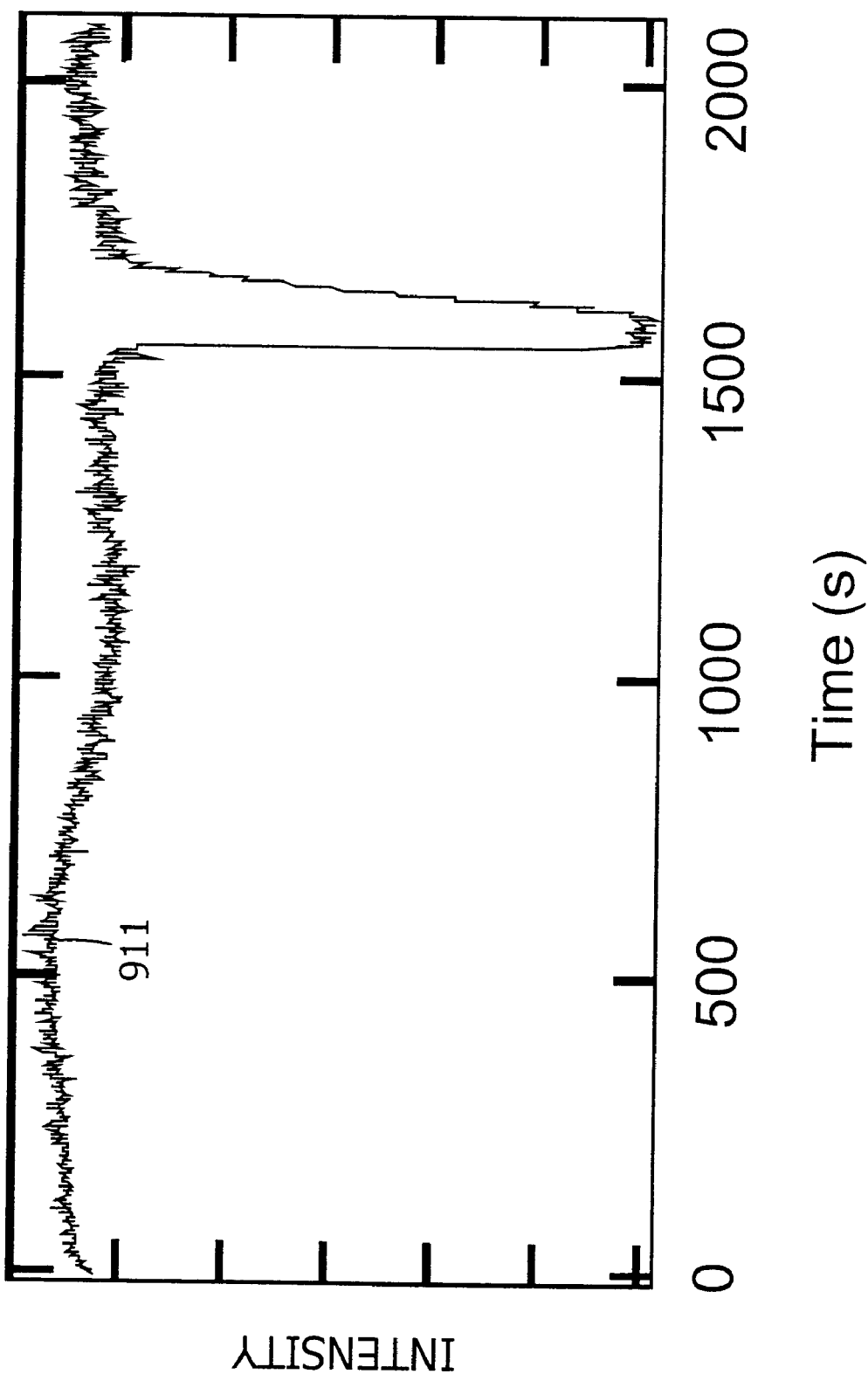
FIG. 12 is a electropherogram of the intensity (y-axis) over time of the average of the five (5) adjacent pixels centered around each maxima pixel, which average corresponds to the average of all five (5) pixels shown in FIG. 11.

Due to this behavior, it has been found that it is clearly advantageous to average substantially concurrent data from multiple adjacent pixels. This averaging accomplishes several things. It yields data with a higher quality baseline of the pixel signals. That is, the long time drifts are minimized or cancel each other out giving a flat baseline of the pixel signals over the duration of the experiment. The short time fluctuations of the pixel signals also cancel out, reducing the noise of the pixel signals and yielding a better pixel signal to noise (S/N) ratio. This is shown in FIGS. 11 and 12. In FIG. 11, the waveforms 901, 903, 905, 907 and 909 illustrate the digital signals of five adjacent pixels shown as a function of time. The S/N ratio for the individual pixels ranges from about 0–10. In FIG. 12, a waveform 911 illustrating the data averaged over all five pixels is shown. The S/N ratio for the averaged data is about 50. Thus, the improvement in the S/N is at least about a factor of 5. If the improvement were a result of only increased signal averaging, one would expect to see a S/N ratio to improve by the square root of the number of points, the square root of five in this case. Thus, these figures indicate that the correlated noise is cancelled by averaging adjacent pixels and yields an additional factor of greater than two (>2) improvement in the S/N ratio. In addition, the averaged data shows a flat baseline of the signals resulting from the cancellation of the long time drift.

Using a five pixel-averaging scheme also increases the robustness of the data interpretation. The averaging scheme can be automatically applied to each peak. This is not the case when using a single pixel. In FIG. 11, the pixel with the highest S/N ratio is not the main pixel shown by waveform 903 and having a S/N ratio of about 5. It is an adjacent pixel shown by waveform 909 and having a S/N ratio of about 10. Thus, the operator would have to search each pixel to find the best data. The five-pixel averaging allows for the data reduction to be automated. This is especially important for an instrument with 96 capillaries operating in a laboratory that expects to do many libraries a day, every day of the week, every week of the year.

When introducing elements of the present invention or the preferred embodiment(s) thereof, the articles "a", "an", "the" and "said" are intended to mean that there are one or more of the elements. The terms "comprising", "including"

and "having" are intended to be inclusive and mean that there may be additional elements other than the listed elements.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A parallel capillary electrophoresis system for separating and analyzing the components of multiple chemical samples, said system comprising a bundle of capillary tubes arrayed to have at least portions of the tubes extending generally parallel to one another in a first plane, each tube being adapted for the flow of a fluid sample therethrough, a power source for applying a potential difference between inlet end portions and outlet end portions of the tubes to cause an electrical current to flow through the contents of the capillary tubes at a level sufficient to cause separation in said fluid samples, a light source for emitting light to pass through said capillary tube portions, a photodetector comprising a linear array of photodetector elements for receiving light passing through said capillary tubes, the light passing through each said capillary tube portions illuminating several photodetector elements, each said photodetector element generating a pixel signal corresponding to the light received by said photodetector element, and an analog to digital converter converting each of the pixel signals into a digital value corresponding to the light received by one of the photodetector elements, the improvement comprising:

a processor receiving the digital values and generating a plurality of output signals corresponding thereto, each output signal being a function of at least two digital values corresponding to the light received by two photodetector elements, respectively, so that the output signals correspond to the light passing through the bundle of capillary tubes; and wherein the processor generates output signals such that each output signal is a function of at least two digital values corresponding to the light passing substantially concurrently through two photodetector elements, respectively.

2. The system as set forth in claim 1 wherein the processor selects one digital value and averages the selected digital value with at least a second digital value to generate averaged values and wherein the output signals are a function of the averaged values.

3. The system as set forth in claim 2 wherein the selected digital value and the second digital value correspond to pixel signals from contiguous photodetector elements.

4. The system as set forth in claim 1 wherein each pixel signal is converted into a sequence of digital values and wherein the processor provides output signals which are a function of the sequence of digital values.

5. The system as set forth in claim 1 wherein the at least two digital values are selected to minimize short time fluctuations or other noise of the pixel signals to generate an improved signal to noise ratio of the pixel signals.

6. A parallel capillary electrophoresis system for separating and analyzing the components of multiple chemical samples, said system comprising a bundle of capillary tubes arrayed to have at least portions of the tubes extending generally parallel to one another in a first plane, each tube being adapted for the flow of a fluid sample therethrough, a power source for applying a potential difference between inlet end portions and outlet end portions of the tubes to cause an electrical current to flow through the contents of the capillary tubes at a level sufficient to cause separation in said fluid samples, a light source for emitting light to pass through said capillary tube portions, a photodetector comprising a linear array of photodetector elements for receiving light passing through said capillary tubes, the light passing through each said capillary tube portions illuminating several photodetector elements, each said photodetector element generating a pixel signal corresponding to the light received by said photodetector element, and an analog to digital converter converting each of the pixel signals into a digital value corresponding to the light received by one of the photodetector elements, the improvement comprising:

a processor receiving the digital values and generating a plurality of output signals corresponding thereto, each output signal being a function of at least two digital values corresponding to the light received by two photodetector elements, respectively, so that the output signals correspond to the light passing through the bundle of capillary tubes; and wherein the processor selects one peak digital value and averages the selected digital value with four digital values which correspond to pixel signals from photodetector elements adjacent to the photodetector element corresponding to the selected peak digital value and wherein the output signals are a function of the averaged values.

7. The system as set forth in claim 6 wherein the selected peak digital value corresponds to the light passing through one capillary tube portion.

8. A parallel capillary electrophoresis system for separating and analyzing the components of multiple chemical samples, said system comprising a bundle of capillary tubes arrayed to have at least portions of the tubes extending generally parallel to one another in a first plane, each tube being adapted for the flow of a fluid sample therethrough, a power source for applying a potential difference between inlet end portions and outlet end portions of the tubes to cause an electrical current to flow through the contents of the capillary tubes at a level sufficient to cause separation in said fluid samples, a light source for emitting light to pass through said capillary tube portions, a photodetector comprising a linear array of photodetector elements for receiving light passing through said capillary tubes, the light passing through each said capillary tube portions illuminating several photodetector elements, each said photodetector element generating a pixel signal corresponding to the light received by said photodetector element, and an analog to digital converter converting each of the pixel signals into a digital value corresponding to the light received by one of the photodetector elements, the improvement comprising:

a processor receiving the digital values and generating a plurality of output signals corresponding thereto, each output signal being a function of at least two digital values corresponding to the light received by two photodetector elements, respectively, so that the output signals correspond to the light passing through the bundle of capillary tubes; and wherein the processor selects one peak digital value and averages the selected digital value with at least a second digital value to generate averaged values and wherein the output signals are a function of the averaged values, and further comprising a display receiving the output signals and generating an electropherograms corresponding thereto.

9. A parallel capillary electrophoresis system for separating and analyzing the components of multiple chemical samples, said system comprising:
- a bundle of capillary tubes arrayed to have at least portions of the tubes extending generally parallel to one another in a first plane, each tube being adapted for the flow of a fluid sample therethrough;
- a power source for applying a potential difference between inlet end portions and outlet end portions of the tubes to cause an electrical current to flow through the contents of the capillary tubes at a level sufficient to cause separation in said fluid samples;
- a light source for emitting light to pass through said capillary tube portions;
- a photodetector comprising a linear array of photodetector elements for receiving light passing through said capillary tubes, said linear array being positioned non-parallel to the first plane, the light passing through each said capillary tube portions illuminating several photodetector elements, each said photodetector element generating a pixel signal corresponding to the light received by said photodetector element;
- an analog to digital converter converting each of the pixel signals into a digital value corresponding to the light received by one of the photodetector elements;
- a processor receiving the digital values and generating a plurality of output signals corresponding thereto, each output signal being a function of at least two digital values corresponding to the light received by two photodetector elements, respectively, so that the output signals correspond to the light passing through the bundle of capillary tubes; and
- wherein each pixel signal is converted into a sequence of digital values and the output signals are a function of an average over time of the sequence of digital values.

10. A parallel capillary electrophoresis system for separating and analyzing the components of multiple chemical samples, said system comprising a bundle of capillary tubes arrayed to have at least portions of the tubes extending generally parallel to one another in a first plane, each tube being adapted for the flow of a fluid sample therethrough, a power source for applying a potential difference between inlet end portions and outlet end portions of the tubes to cause an electrical current to flow through the contents of the capillary tubes at a level sufficient to cause separation in said fluid samples, a light source for emitting light to pass through said capillary tube portions, a photodetector comprising a linear array of photodetector elements for receiving light passing through said capillary tubes, the light passing through each said capillary tube portions illuminating several photodetector elements, each said photodetector element generating a pixel signal corresponding to the light received by said photodetector element, and an analog to digital converter converting each of the pixel signals into a digital value corresponding to the light received by one of the photodetector elements, the improvement comprising:
- a processor receiving the digital values and generating a plurality of output signals corresponding thereto, each output signal being a function of at least two digital values corresponding to the light received by two photodetector elements, respectively, so that the output signals correspond to the light passing through the bundle of capillary tubes; and
- wherein the at least two digital values are selected to minimize long time drifts of the pixel signals to generate a substantially flat baseline of the pixel signals.

11. A method of processing a plurality of pixel signals, each generated by one element of an array of photodetector elements illuminated by light passing through a bundle of capillary tubes during a multiplexed capillary electrophoresis process, said method comprising:
- converting each of the pixel element signals into a digital value corresponding to the light received by one of the photodetector elements;
- selecting, for each capillary tube, at least two digital values corresponding to the light received by two photodetector elements; and
- generating output signals corresponding to the light passing through the bundle of capillary tubes, each output signal being a function of the selected digital values, wherein each output signal is a function of at least two digital values corresponding to the light passing substantially concurrently through two photodetector elements, respectively.

12. The method as set forth in claim 11 comprising selecting one digital value and averaging the selected digital value with at least a second digital value to generate averaged values and wherein the output signals are a function of the averaged values.

13. The method as set forth in claim 12 wherein the selected digital value and the second digital value correspond to pixel signals from contiguous photodetector elements.

14. The method as set forth in claim 11 wherein each pixel signal is converted into a sequence of digital values and wherein the output signals are a function of the sequence of digital values.

15. The method as set forth in claim 11 wherein the at least two digital values are selected to minimize short time fluctuations or other noise of the pixel signals to generate an improved signal to noise ratio of the pixels signals.

16. A method of processing a plurality of pixel signals, each generated by one element of an array of photodetector elements illuminated by light passing through a bundle of capillary tubes during a multiplexed capillary electrophoresis process, said method comprising:
- converting each of the pixel element signals into a digital value corresponding to the light received by one of the photodetector elements;
- selecting, for each capillary tube, at least two digital values corresponding to the light received by two photodetector elements;
- generating output signals corresponding to the light passing through the bundle of capillary tubes, each output signal being a function of the selected digital values; and
- selecting one peak digital value and averaging the selected digital value with four digital values which correspond to pixel signals from photodetector elements adjacent to the photodetector element corresponding to the selected peak digital value and wherein the output signals are a function of the averaged values.

17. The method as set forth in claim 16 wherein the selected peak digital value corresponds to the light passing through one capillary tube portion.

18. A method of processing a plurality of pixel signals, each generated by one element of an array of photodetector elements illuminated by light passing through a bundle of capillary tubes during a multiplexed capillary electrophoresis process, said method comprising:
- converting each of the pixel element signals into a digital value corresponding to the light received by one of the photodetector elements;

selecting, for each capillary tube, at least two digital values corresponding to the light received by two photodetector elements;

generating output signals corresponding to the light passing through the bundle of capillary tubes, each output signal being a function of the selected digital values; and selecting one peak digital value and averaging the selected digital value with at least a second digital value to generate averaged values and wherein the output signals are a function of the averaged values, and further comprising displaying an electropherograms corresponding to the output signals.

19. A method of processing a plurality of pixel signals, each generated by one element of an array of photodetector elements illuminated by light passing through a bundle of capillary tubes during a multiplexed capillary electrophoresis process, said bundle of capillary tubes arrayed to have at least portions of the tubes extending generally parallel to one another in a first plane, said method comprising:

positioning the array of photodetector elements non-parallel to the first plane;

converting each pixel signal into a sequence of digital values;

a digital value corresponding to the light received by one of the photodetector elements;

selecting, for each capillary tube, at least two digital values corresponding to the light received by two photodetector elements; and generating output signals corresponding to the light passing through the bundle of capillary tubes, wherein the output signals are a function of an average over time of the sequence of digital values.

20. A method of processing a plurality of pixel signals, each generated by one element of an array of photodetector elements illuminated by light passing through a bundle of capillary tubes during a multiplexed capillary electrophoresis process, said method comprising:

converting each of the pixel element signals into a digital value corresponding to the light received by one of the photodetector elements;

selecting, for each capillary tube, at least two digital values corresponding to the light received by two photodetector elements, wherein the at least two digital values are selected to minimize long time drifts of the pixel signals to generate a substantially flat baseline of the pixel signals; and generating output signals corresponding to the light passing through the bundle of capillary tubes, each output signal being a function of the selected digital values.

21. A parallel capillary electrophoresis system for separating and analyzing the components of multiple chemical samples, said system comprising:

a bundle of capillary tubes arrayed to have at least portions of the tubes extending generally parallel to one another in a first plane, each tube being adapted for the flow of a fluid sample therethrough;

a power source for applying a potential difference between inlet end portions and outlet end portions of the tubes to cause an electrical current to flow through the contents of the capillary tubes at a level sufficient to cause separation in said fluid samples;

a light source for emitting light to pass through said capillary tube portions;

a photodetector comprising a linear array of photodetector elements for receiving light passing through said capillary tubes, said linear array being positioned non-parallel to the first plane, the light passing through each said capillary tube portions illuminating several photodetector elements, each said photodetector element generating a pixel signal corresponding to the light received by said photodetector element;

an analog to digital converter converting each of the pixel signals into a digital value corresponding to the light received by one of the photodetector elements; and a processor receiving the digital values and generating a plurality of output signals corresponding thereto, each output signal being a function of at least two digital values corresponding to the light received by two photodetector elements, respectively, so that the output signals correspond to the light passing through the bundle of capillary tubes.

22. A system as set forth in claim 21 wherein the linear array is positioned generally perpendicular to the first plane.

23. A system as set forth in claim 21 wherein the processor generates output signals such that each output signal is a function of at least two digital values corresponding to the light passing substantially concurrently through two photodetector elements, respectively.

* * * * *